United States Patent
Hemmerle

(10) Patent No.: US 12,377,161 B2
(45) Date of Patent: *Aug. 5, 2025

(54) TNF-ALPHA IMMUNOCONJUGATE THERAPY FOR THE TREATMENT OF BRAIN TUMORS

(71) Applicant: PHILOGEN S.P.A, Siena (IT)

(72) Inventor: Theresa Hemmerle, Otelfingen (CH)

(73) Assignee: PHILOGEN S.P.A., Siena (IT)

( * ) Notice: Subject to any disclaimer, the term of this patent is extended or adjusted under 35 U.S.C. 154(b) by 0 days.

This patent is subject to a terminal disclaimer.

(21) Appl. No.: 18/480,153

(22) Filed: Oct. 3, 2023

(65) Prior Publication Data

US 2024/0197903 A1 Jun. 20, 2024

Related U.S. Application Data

(63) Continuation of application No. 17/999,444, filed as application No. PCT/EP2021/063758 on May 24, 2021, now Pat. No. 11,872,288.

(30) Foreign Application Priority Data

May 22, 2020 (EP) .................................... 20176157

(51) Int. Cl.
*A61K 39/00* (2006.01)
*A61K 39/395* (2006.01)
*A61K 47/68* (2017.01)
*A61P 35/00* (2006.01)

(52) U.S. Cl.
CPC .......... *A61K 47/6813* (2017.08); *A61P 35/00* (2018.01); *A61K 2039/505* (2013.01)

(58) Field of Classification Search
None
See application file for complete search history.

(56) References Cited

U.S. PATENT DOCUMENTS

| | | | |
|---|---|---|---|
| 11,872,288 B2 * | 1/2024 | Hemmerle | C07K 16/18 |
| 2012/0288473 A1 | 11/2012 | Sampson | |
| 2020/0253943 A1 | 8/2020 | Bernardes et al. | |

FOREIGN PATENT DOCUMENTS

| | | |
|---|---|---|
| CN | 1612895 A | 5/2005 |
| CN | 101437847 A | 5/2009 |
| EP | 0 120 694 A2 | 10/1984 |
| EP | 0 125 023 A1 | 11/1984 |
| WO | 92/01047 A1 | 1/1992 |
| WO | 01/62298 A2 | 8/2001 |
| WO | 03/076469 A2 | 9/2003 |
| WO | 2005/023318 A1 | 3/2005 |
| WO | 2006/026348 A1 | 3/2006 |
| WO | 2018/011404 A1 | 1/2018 |

OTHER PUBLICATIONS

Borsi et al. Selective targeted delivery of TNF to tumor blood vessels. Blood. 2003;102:4384-4392. (Year: 2003).*
Oshiro et al. Evaluation of intratumoral administration of tumor necrosis factor-alpha in patients with malignant glioma. Anticancer Res . Nov.-Dec. 2006;26(6A):4027-32. (Year: 2006).*
Albrecht et al. Anticalins directed against the fibronectin extra domain B as diagnostic tracers for glioblastomas. Int. J. Cancer: 138, 1269-1280 (2016). (Year: 2016).*
Saw et al. Aptide-conjugated liposome targeting tumor-associated fibronectin for glioma therapy. J. Mater. Chem. B, 2013, 1, 4723-4726. (Year: 2013).*
Spaeth et al. Radioimmunotherapy targeting the extra domain B of fibronectin in C6 rat gliomas: a preliminary study about the therapeutic efficacy of iodine-131-labeled SIP(L19). Nuclear Medicine and Biology 33 (2006) 661-666. (Year: 2006).*
Yamini et al. Adenovirally Delivered Tumor Necrosis Factor-A Improves the Antiglioma Efficacy of Concomitant Radiation and Temozolomide Therapy. Clin Cancer Res 2007;6217 13(20). (Year: 2007).*
Parisi et al. Temozolomide and Radiotherapy versus Radiotherapy Alone in High Grade Gliomas: A Very Long Term Comparative Study and Literature Review. Biomed Res Int. 2015; 2015: 620643. (Year: 2015).*
Glas, M et al. (2009). Long-term survival of glioblastoma patients treated with radiotherapy and lomustine plus temozolomide. Journal of Clinical Oncology, 27(8):1257-1261. (Year: 2009).*
International Search Report, mailed Oct. 8, 2021, issued in corresponding International Application No. PCT/EP2021/063758.
Roth, Patrick et al., "Targeting glioblastoma with novel immunocytokines," Journal of Clinical Oncology, vol. 38, No. 15_suppl, May 20, 2020, p. 2558-2558.
Weiss, Tobias et al., " History of Changes for Study: NCT03779230 Version 3," Jun. 25, 2019, Retrieved from the Internet: URL:https://clinicaltrials.gov/ct2/history/NCT03779230?V 3=View#StudyPageTop, Retrieved on Jun. 30, 2021.
Weiss, Tobias et al., "Immunocytokines are a promising immunotherapeutic approach against glioblastoma," Science Translational Medicine, vol. 12, No. 564, Oct. 7, 2020, eabb2311, pp. 1-11.
Written Opinion of the International Searching Authority, completed Jul. 31, 2021, issued in corresponding International Application No. PCT/EP2021/063758.
International Preliminary Report on Patentability, completed Dec. 6, 2021, issued in corresponding International Application No. PCT/EP2021/063758.
Notice of Reasons for Rejection, dated Apr. 12, 2023, issued in corresponding Japanese Patent Application No. 2022-570616.
Puca, E. et al., "Comparative evaluation of bolus and fractionated administration modalities for two antibody-cytokine fusions in immunocompetent tumor-bearing mice," Journal of Controlled Release, vol. 317, Nov. 2019, pp. 282-290.

(Continued)

*Primary Examiner* — Maher M Haddad
(74) *Attorney, Agent, or Firm* — Howson & Howson LLP; Kathleen D. Rigaut; Richard F. Kane

(57) ABSTRACT

The present invention relates to immunoconjugates, compositions, methods and uses for treating brain tumors, especially glioma, by administration of a tumour necrosis factor alpha (TNFα) immunoconjugate.

16 Claims, 4 Drawing Sheets

Specification includes a Sequence Listing.

(56) References Cited

OTHER PUBLICATIONS

Corbellari, R. et al., "The immunocytokine L19-TNF eradicates Sarcomas in combination with Chemotherapy agents or with immune check-point inhibitors," bioRxiv, Feb. 4, 2020, pp. 1-24.

Menssen, H.D. et al., "Antibody-based delivery of tumor necrosis factor (L19-TNFα) and interleukin-2 (L19-IL2) to tumor-associated blood vessels has potent immunological and anticancer activity in the syngeneic J558L BALB/c myeloma model," Journal of Cancer Research and Clinical Oncology, vol. 144, 2018, pp. 499-507.

First Office Action, dated Jul. 29, 2023, issued in corresponding Chinese Patent Application No. 2202180036945.7.

Xiong Fangwu et al., "Lomustine," Chinese Clinical Drug Dictionary (Chemical Medicine) (1st volume), published Aug. 31, 2018, China Medical Science and Technology Press.

NextSource Biotechnology LLC. (2018). Gleostine carmustine capsule gelatin coated: Highlights of prescribing information, pp. 1-16.

NextSource Biotechnology LLC. (2016). NextSource Biotechnology Gains FDA Approval for New 5 mg Strength of Gleostine® (Lomustine), an Anti-Cancer Chemotherapy Agent, pp. 1-3.

NextSource Biotechnology LLC. (2014). NextSource Biotechnology Announces FDA Short Supply release of the formally known Bristol Myers Squibb (CeeNu®) Brand Oncology product now currently marketed under the NextSourceBiotechnology Lomustine (CCNU) label Exclusively in the United States, pp. 1-4.

Clinical Trials NCT03779230Safety and Efficacy of L19TNF in Patients With Isocitrate Dehydrogenase (IDH) Wildtype WHO Grade III / IV Glioma at First Re(GLIOMOON). Mar. 19, 2019, pp. 1-5.

Weiss et al, "Immunocytokines are a novel immunotherapeutic approach against glioblastoma," Neuro-Oncology, vol. 21, (supp 3), Aug. 2019, pp. iii61. Abstract No. P12.08.

Look et al., "Lomustine and the Immunocytokine L 19TNF Are a Promising Treatment Combination for Recurrent Glioblastoma," abstract OS08.7.A., Neuro-Oncology, vol. 24, No. Supplement_2, Sep. 2022, pp. ii19-ii20.

Look et al., "The Combination of Lomustine and the Immunocytokine L 19TNF is a Promising Treatment for Recurrent Glioblastoma," Abstract CTIM-22, Neuro-Oncology (IF 15.9), Pub Date: Nov. 14, 2022.

\* cited by examiner

Figure 1A
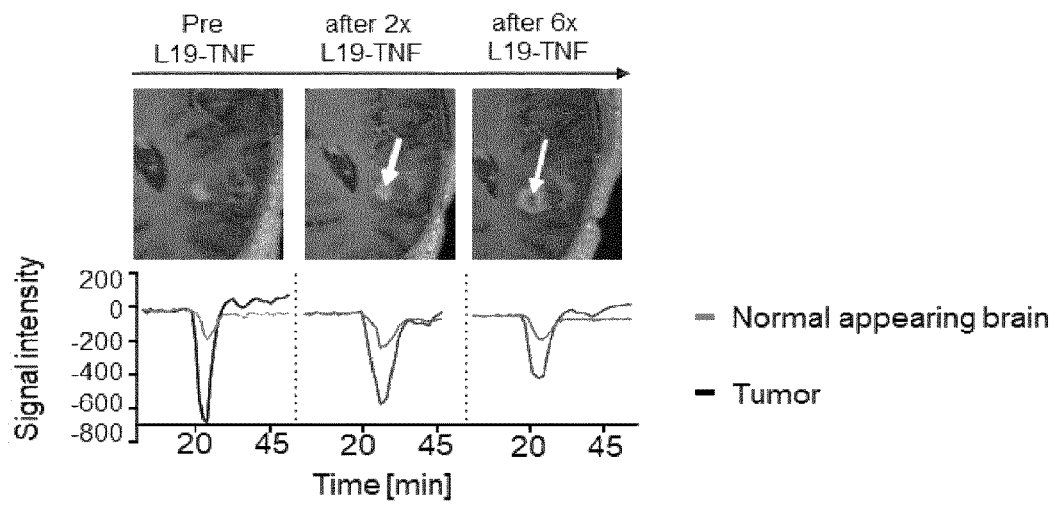
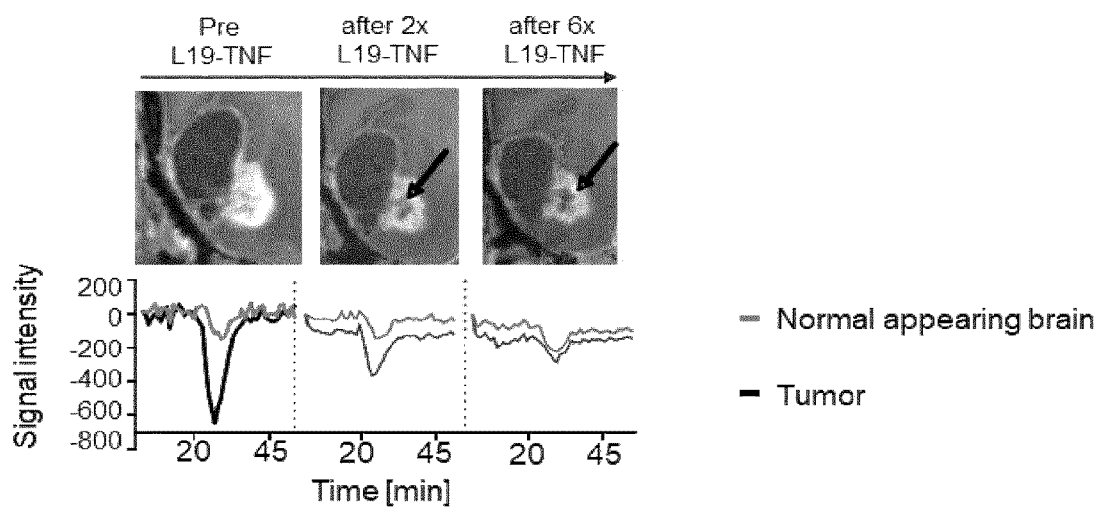

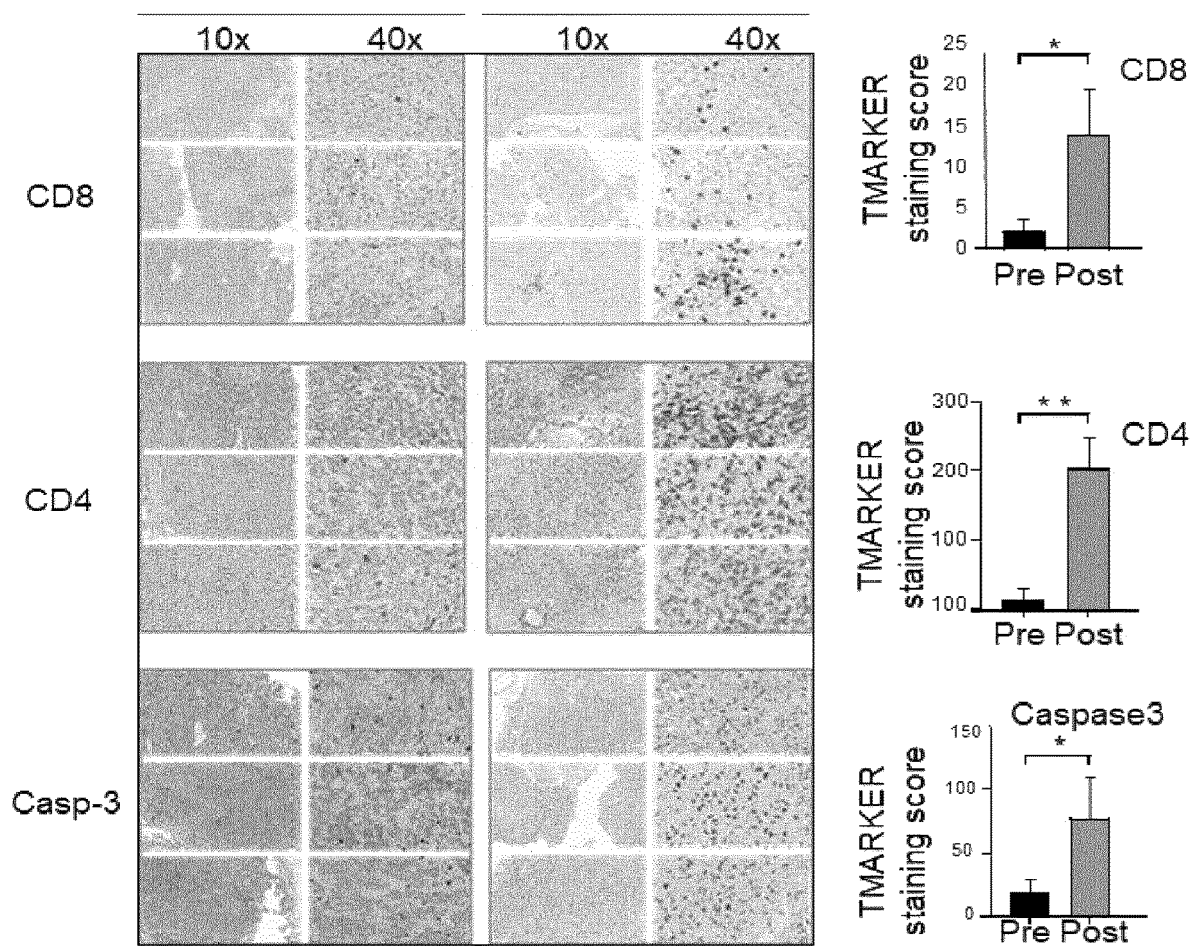

Figure 2

VH (SEQ ID NO: 7)

CDR1                        CDR2

EVQLLESGGGLVQPGGSLRLSCAASGFTFS<u>SFSMS</u>WVRQAPGKGLEWVS<u>SISGSS</u>

CDR3

<u>GTTYYADSVKG</u>RFTISRDNSKNTLYLQMNSLRAEDTAVYYCAK<u>PFPYFDY</u>WGQGT

LVTVSS

LINKER (SEQ ID NO: 8)

GDGSSGGSGGAS

VL (SEQ ID NO: 9)

CDR1                        CDR2

EIVLTQSPGTLSLSPGERATLSC<u>RASQSVSSSFLA</u>WYQQKPGQAPRLLIY<u>YASSR</u>

CDR3

<u>AT</u>GIPDRFSGSGSGTDFTLTISRLEPEDFAVYYC<u>QQTGRIPPT</u>FGQGTKVEIK

Figure 3
A.
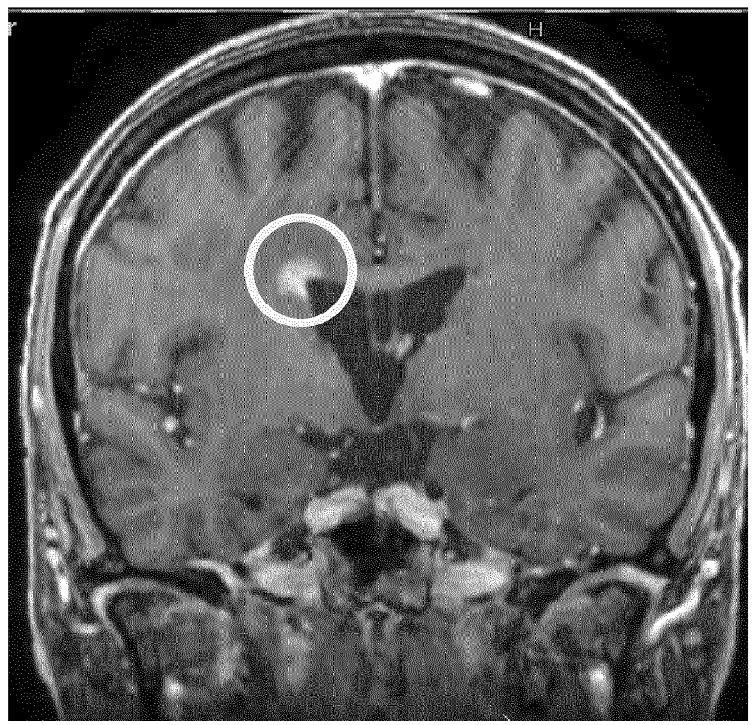
B.
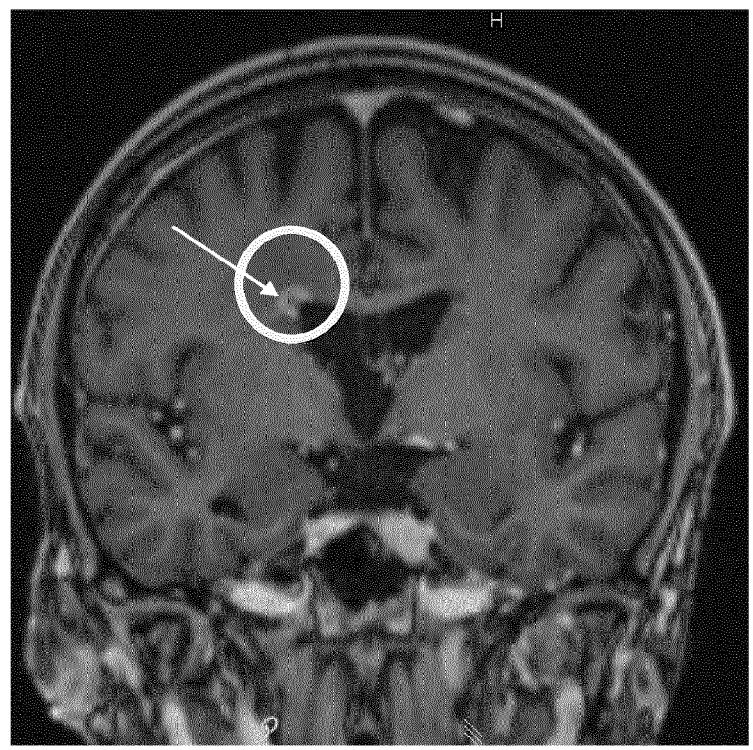

TNF-ALPHA IMMUNOCONJUGATE THERAPY FOR THE TREATMENT OF BRAIN TUMORS

CROSS REFERENCE TO RELATED APPLICATION

This application is a Continuation of U.S. application Ser. No. 17/999,444, filed Nov. 21, 2022, which is a § 371 of International Application No, PCT/US2021/063758, filed May 24, 2021, which claims priority to EP Application No. 20176157.4 filed May 22, 2020, the entire disclosure of each being incorporated herein by reference as though set forth in full.

REFERENCE TO AN ELECTRONIC SEQUENCE LISTING

The contents of the electronic sequence listing (MEW-113-US01.xml; 18, 174 bytes; and Date of Creation: Oct. 2, 2023) is herein incorporated by reference in its entirety.

FIELD OF THE INVENTION

The present invention relates to immunoconjugates, compositions, methods and uses for treating brain tumors, especially glioma, by administration of a tumour necrosis factor alpha (TNFα) immunoconjugate.

BACKGROUND TO THE INVENTION

Brain tumors comprise primary and secondary tumors. Primary brain tumors are neoplasms that originate from cells of the brain or meninges, in contrast to secondary brain tumors such as brain metastases or malignant lymphomas (PCNSL), which originate outside the central nervous system (CNS).

Glioma is a type of tumor that occurs in the brain and spinal cord and starts in the glial cells of the brain or the spine. A glioma can affect brain function and be live threatening, depending on its location and rate of growth. Gliomas along with meningiomas, are the most common types of primary brain tumors. They are classified histologically according to the type of glial cell involved in the tumorigenesis (astrocytes, oligodendrocytes, ependymal cells) and molecularly according to genetic features, which can help predict how the tumor will behave over time and which treatments are most likely to work.

Gliomas are graded according to the four-tiered WHO system ranging from grade I to IV, indicating malignancy.
  Grade I: slow growing, well-demarcated tumors with favourable prognosis
  Grade II: slow growing tumors often with brain invasive growth that precludes complete resection
  Grade III: rapidly growing high-grade tumors with features of anaplasia, particularly high cellularity, cellular pleomorphism, increased nuclear atypia and brisk mitotic activity
  Grade IV ("glioblastoma"): most malignant gliomas which show the characteristics of grade III and additional pathological microvascular proliferation and areas of necrosis.

The cornerstone of glioma therapy is the greatest possible but non-functional resection, which can be curative in the case of WHO grade I glioma. For diffuse WHO grade II to IV gliomas, a macroscopically complete resection is often possible, but the diffuse infiltrating character of the disease means that this is usually not a curative resection. In gliomas, the extent of resection is a prognostic factor. Postoperative radiotherapy (RT) improves survival, the time of RT may vary according to risk factors and WHO grade. The third pillar of therapy is drug-based tumor therapy. Predictive markers are LOH1p/19q status and MGMT promoter methylation.

A variety of treatments including radiotherapy or radiosurgery, surgery, chemotherapy or combination of these options as well as supportive care are available for patients with no response or progression after initial therapy, but survival is highly variable on an individual basis. Patients with adequate performance status that have not received prior cytotoxic therapy may benefit from chemotherapy. Upon tumor recurrence, treatment options include supportive care, reoperation, re-irradiation, systemic therapies and combined modality therapy. Several options are available for second-line chemotherapy, but no standard of care has been established.

Despite the available therapy options, glioma remains a life-threatening disease. While the 5-year relative survival rate for all cancers combined in the United States was 69% between 2008 and 2014, the 5-year relative survival rate for brain and other nervous system cancers in the same period was only 35%. High grade glioma and especially glioblastoma is one of the most challenging to treat cancers with a very poor prognosis and a median survival in the range of only 16 months with standard of care treatment. Because of the poor prognosis and the limited treatment options for these patients, novel treatment options are urgently needed.

Tumour necrosis factor alpha (TNFα) is a cytokine produced by many cell types, mainly activated monocytes and macrophages. It is expressed as a 26 kDa integral transmembrane precursor protein from which a mature protein of approximately 17 kDa is released by proteolytic cleavage. The soluble bioactive TNFα is a homotrimer that binds cell surface receptors. TNFα has been shown to induce necrosis of solid tumours. It exerts its effects mainly on the endothelium of the tumour-associated vasculature, with increased permeability, upregulation of tissue factor, fibrin deposition and thrombosis, and massive destruction of the endothelial cells.

WO2001/062298, which is hereby incorporated by reference in its entirety, described immunoconjugates comprising TNFα, fused to antibody L19. L19 specifically binds the ED-B domain of fibronectin isoform B-FN, which is one of the best-known markers of angiogenesis (U.S. Pat. No. 8,097,254). ED-B is an extra domain of 91 amino acids found in the B-FN isoform and is identical in mouse, rat, rabbit, dog and man. B-FN accumulates around neovascular structures in aggressive tumours and other tissues undergoing angiogenesis, such as the endometrium in the proliferative phase and some ocular structures in pathological conditions but is otherwise undetectable in normal adult tissues.

SUMMARY OF THE INVENTION

The present inventors have determined that the administration of immunoconjugates comprising TNFα and can be used to successfully treat brain tumors.

Accordingly, one aspect of the invention provides a method of treating a brain tumor by administering a TNFα immunoconjugate to the patient.

In another aspect, the invention provides a TNFα immunoconjugate for use in a method of treating a brain tumor in a patient, the method comprising administering the TNFα immunoconjugate to the patient.

In yet another aspect, the invention provides the use of a TNFα immunoconjugate in the manufacture of a medicament for the treatment of a brain tumor in a patient, the treatment comprising administering the TNFα immunoconjugate.

In preferred embodiments, the brain tumor is a glioma. The glioma may be a Grade III/IV glioma. The glioma may be an isocitrate dehydrogenase (IDH) wildtype glioma. In some embodiments, the Grade III/IV glioma is at first relapse when the treatment is administered. In some embodiments, the glioma is a Grade IV glioblastoma. Optionally, the Grade IV glioblastoma may be newly diagnosed when the treatment is administered. Optionally, the Grade IV glioblastoma may be at first relapse when the treatment is administered.

In preferred embodiments, the TNFα immunoconjugate comprises TNFα linked to an antibody molecule that binds to a splice isoform of an extracellular matrix component. The splice isoform of fibronectin may be B-FN.

In preferred embodiments, the TNFα immunoconjugate comprises TNFα linked to an antibody molecule comprising L19 complementarity determining regions (CDRs), wherein the amino acid sequences of the CDRs correspond with those set forth in SEQ ID NOs: 1-6. In some embodiments, the antibody molecule comprises the L19 VH domain SEQ ID NO: 7 and the L19 VL domain SEQ ID NO: 9. In some embodiments, the TNFα immunoconjugate comprises TNFα linked to an antibody molecule which is a single chain Fv (scFv), optionally wherein the antibody molecule is L19 (scFv) SEQ ID NO: 10. The TNFα immunoconjugate may have the amino acid sequence of SEQ ID NO: 13.

The treatments disclosed herein typically involve the administration of the immunoconjugate by intravenous injection. Alternatively, the immunoconjugate can be administered by intratumoural or intrathecal injection.

In addition to immunoconjugate administration, in some embodiments, the immunoconjugate is administered in combination with radiotherapy and/or in combination with another anticancer agent, e.g. a chemotherapy.

In some embodiments, the immunoconjugate is administered in combination with a chemotherapy. The chemotherapy may be an alkylating agent. The alkylating agent may be lomustine. The lomustine may be administered at a dose that is within the range of 50-200 mg/m$^2$, or 75-150 mg/m$^2$. The lomustine may be administered at a dose of about 80, about 90, about 100, or about 110 mg/m$^2$. Preferably, lomustine is administered at a dose of between about 90 and about 110 mg/m$^2$. In some embodiments, the lomustine is administered at a dose of about 90 mg/m$^2$. Combination therapies involving lomustine may be particularly useful for treating a glioblastoma at first relapse.

In some embodiments, the chemotherapy (alkylating agent) is temozolomide (TMZ). The TMZ may be administered at a dose that is within the range of 50-300 mg/m$^2$, or 75-200 mg/m$^2$. Combination treatments, e.g. those involving TMZ, may involve radiotherapy as well. For instance, the radiotherapy can be administered at daily fractions of 2 Gy (a total of 60 Gy in 30 fractions). When TMZ is administered in combination with radiotherapy, TMZ it is preferably administered at 75 mg/m$^2$ or at doses between 150 and 200 mg/m$^2$ in the maintenance setting. Combination therapies involving TMZ and radiotherapy may be particularly useful for treating a newly diagnosed glioblastoma.

When administered in combination with lomustine, L19-TNFα can be given at doses between 5 and 20 µg/Kg, preferably between 8 and 15 µg/Kg, more preferably between 10 and 13 µg/Kg. When administered in combination with TMZ, L19-TNFα can be given at doses of between 5 and 20 µg/Kg, preferably between 6 and 15 µg/Kg, more between 7 and 13 µg/Kg.

When administered without chemotherapy (i.e., as a monotherapy, or in combination with radiotherapy alone), L19-TNFα can be given at doses between 5 and 20 µg/Kg, preferably between 6 and 18 µg/Kg, between 7 and 17 µg/Kg or between 8 and 15 µg/Kg, more preferably between 10 and 13 µg/Kg.

The skilled person will understand that the TNFα immunoconjugate may be administered just once in the context of the medical uses and treatments of the present invention. Alternatively, the medical uses and treatments of the present invention may involve multiple administrations of the TNFα immunoconjugate. In some embodiments, the medical uses and treatments of the present invention may involve chemotherapy, radiotherapy and/or surgery (each of which may be performed before, concurrently with, or after TNFα immunoconjugate administration).

In some embodiments, following the medical uses and/or treatments of the present invention (which involve the TNFα immunoconjugate being administered to the patient, as disclosed herein), tumor necrosis can be observed after TNFα immunoconjugate administration. In some cases, tumor necrosis is detectable a day after the TNFα immunoconjugate was administered. Thus, the medical uses and methods of the invention can optionally include the step of sending the patient for an evaluation of tumor necrosis at a timepoint after TNFα immunoconjugate administration, e.g. 1 day after, 2 days after, 3 days after, 4 days after, 5 days after, 6 days after, about a week after, about 10 days after, about two weeks after or about a month after the TNFα immunoconjugate is administered. Thus, the medical uses and methods of the invention can also include taking a decision regarding further therapy, and optionally performing said further therapy, after viewing the results of the evaluation of tumor necrosis. Preferably, tumor necrosis will be observed at one or more of these time points. The skilled person is readily able to use techniques such as perfusion MRI to measure tumor necrosis. Perfusion MRI can discriminate between dead tumor areas and live regions of tumor cells; this technique can be applied to the present clinical setting. Further therapy may comprise further administration of the medical uses and/or treatments of the present invention. Additionally, or alternatively, further therapy may comprise chemotherapy, radiotherapy and/or surgery.

In some embodiments, following the medical uses and/or treatments of the present invention (which involve the TNFα immunoconjugate being administered to the patient, as disclosed herein), a reduction of blood perfusion to the tumor can be observed after TNFα immunoconjugate administration. In some cases, a reduction of blood perfusion to the tumor is detectable a day after the TNFα immunoconjugate is administered to the patient. Thus, the medical uses and methods of the invention can optionally include the step of sending the patient for observation of tumor blood perfusion at a timepoint after TNFα immunoconjugate administration, e.g. 1 day after, 2 days after, 3 days after, 4 days after, 5 days after, 6 days after, about a week after, about 10 days after, about two weeks after or about a month after the TNFα immunoconjugate is administered. Preferably, a reduction of blood perfusion will be observed at one or more of these time points. The medical uses and methods of the invention can also include the subsequent step of taking a decision regarding further therapy, and optionally performing said further therapy, after viewing the results of the tumor blood perfusion observation. The skilled person is readily able to use techniques such as perfusion MRI to perform this observation. Perfusion MRI is a common method of monitoring brain tumors; and can be applied to the present clinical setting. Further therapy may comprise further administration of the medical uses and/or treatments of the present invention. Additionally, or alternatively, further therapy may comprise chemotherapy, radiotherapy and/or surgery.

In some embodiments of the medical uses and/or treatments of the present invention (which involve the TNFα immunoconjugate being administered to the patient, as disclosed herein), surgery can be performed on the brain tumor. In some embodiments, some of the tumor has been removed prior to the medical use/method of the present invention being performed. In some embodiments, some, or all of the tumor will be removed after the medical uses and/or treatments of the present invention are performed.

In some embodiments, following the medical uses and/or treatments of the present invention (which involve the TNFα immunoconjugate being administered to the patient, as disclosed herein), infiltration of T cells into the tumor tissue can be observed after TNFα immunoconjugate administration. The detection of T cell infiltration can be achieved by immunohistochemistry performed on a tumor sample obtained via surgery. The infiltrating T cells may be CD4+ T cells (so called 'helper T cells') and/or CD8+ T cells (so called 'cytotoxic T cells'). In some embodiments of the invention, surgery precedes and follows TNFα immunoconjugate administration (e.g. with chemo/radiotherapy). In these embodiments, the extent of T cell infiltration before TNFα immunoconjugate administration can be compared with the extent of T cell infiltration after TNFα immunoconjugate administration. In some embodiments, the increase of T cell infiltration can be observed in CD4+ T cell count. In some embodiments, the increase of T cell infiltration can be observed in CD8+ T cell count. The skilled person is readily able to use techniques such as immunohistochemistry, or flow cytometry, to detect and count T cells in a sample. Appropriate reagents are widely available. Such techniques involve using anti-T cell antibodies to stain the T cells in a mixed-cell sample.

A number of splice isoforms of tumour extracellular matrix components are known, and antibody molecules targeting any such isoform may be used to selectively target the cancer. These include splice isoforms of fibronectin, such as B-FN. B-FN includes an extra domain ED-B, and antibody molecules of the invention are preferably targeted to this domain. A preferred antibody molecule comprises the complementarity determining regions (CDRs) of antibody L19. These are, as illustrated in FIG. 2:

VH CDR 1
SEQ ID NO: 1
SFSMS

VH CDR 2
SEQ ID NO: 2
SISGSSGTTYYADSVKG

VH CDR 3
SEQ ID NO: 3
PFPYFDY

VL CDR 1
SEQ ID NO: 4
RASQSVSSSFLA

VL CDR 2
SEQ ID NO: 5
YASSRAT

VL CDR 3
SEQ ID NO: 6
QQTGRIPPT

The TNFα immunoconjugate preferably comprises TNFα linked to an antibody molecule comprising the L19 CDRs. The antibody molecule in the immunoconjugate may bind the same extracellular matrix component, optionally the same splice isoform, e.g. they may bind the same domain.

Preferably, the antibody molecule (of the TNFα immunoconjugate) comprises the L19 VH domain and/or the L19 VL domain. Amino acid sequences of the L19 VH and VL domains are SEQ ID NO: 7 and SEQ ID NO: 9 respectively (FIG. 2).

Preferably the antibody molecule is a single chain Fv (scFv) or other antibody fragment of low molecular weight and/or lacking an Fc region. These properties assist with targeting and tissue penetration of the immunoconjugate at the tumour site. A preferred antibody molecule is scFv-L19, which is an scFv comprising an L19 VH domain and an L19 VL domain, wherein the VH and VL are conjoined in a single polypeptide chain by a peptide linker sequence. The skilled person will appreciate that a wide range of linkers can be used both within the context of linking VH and VL domains; and within the context of linking the antibody domain to the TNF domain. The skilled person can readily identify linkers that can be used to retain the functionality of the domains that they are linking. The VH domain contains VH CDR1, CDR2 and CDR3 sequences, and the VL domain contains VL CDR1, CDR2 and CDR3 sequences. The VH domain may have an amino acid sequence as set out in FIG. 2 (SEQ ID NO: 7). The VL domain may have an amino acid sequence as set out in FIG. 2 (SEQ ID NO: 9). The VH and VL domains are normally joined by a peptide linker such as the 12-residue linker shown in FIG. 2 (SEQ ID NO: 8). Preferably, the scFv-L19 comprises or consists of the amino acid sequence shown in FIG. 2 (SEQ ID NO: 10).

A molecular linker such as a peptide may be used to join the cytokine to the antibody molecule, facilitating expression of all or part of the immunoconjugate as a fusion protein. Where the antibody molecule is also a single chain molecule, such as scFv, the entire immunoconjugate polypeptide chain may conveniently be produced as a fusion protein. For the TNFα immunoconjugate, the fusion proteins are then assembled into trimers, allowing TNFα to adopt its normal trimeric form.

Optionally, the immunoconjugate carries a detectable and/or functional label, such as a radioactive isotope. Radiolabelled L19, and its use in cancer therapy, has been previously described (WO2003/076469, WO2005/023318).

Optionally, the immunoconjugates are injected directly at the cancer site, i.e. at the tumour/lesion responsible for causing the cancer. In some aspects, the injection needle is inserted through an intracranial route to access the lesion.

Other treatments that may be used in combination with the invention include the administration of chemotherapy and/or radiotherapy.

In some aspects, the chemotherapy is the alkylating agent temozolomide (TMZ) or lomustine. TMZ may be administered at 75-200 mg/m². The lomustine may be administered at a dose that is within the range of 50-200 mg/m², or 75-150 mg/m². The lomustine may be administered at a dose of about 80, about 90, about 100 or about 110 mg/m². Preferably, lomustine may be administered at 90 mg/m².

In some other aspects, radiotherapy may be administered at 20-100 Gy, preferably 40-80 Gy, more preferably at 60 Gy. The radiotherapy may be fractionated. For instance, the dose may be split into fractions of about 2 Gy. In some embodiments, the radiotherapy is administered at 60 Gy/30 fractions given at 2 Gy on Days 1-5 of each week of treatment, for 6 weeks of treatment.

DESCRIPTION OF THE DRAWINGS

FIG. 1A shows glioma lesions in two different patients before and after treatment with L19-TNFα. The lesions gradually shrink after two and six cycles. The dark inner part of the lesions indicates the expanding necrotic core, confirming the therapeutic action of targeted TNFα.

FIG. 1B Immunohistochemistry analysis before and after treatment with L19-TNFα. The increase in tumor-infiltrating CD4 and CD8 T-cells after treatment confirmed the therapeutic action of targeted TNFα. Similarly, the increase of caspase-3 indicates a higher number of dead tumor cells.

FIG. 2 shows the amino acid sequence of L19(scFv) (SEQ ID NO: 10). The VH and VL domains are shown separately (SEQ ID NO: 7 and SEQ ID NO: 9, respectively). The CDR 1, 2 and 3 sequences in both the VH and VL domains are shown underlined. The VH and VL domains are linked by a 12-residue peptide linker sequence (SEQ ID NO: 8).

FIG. 3 shows MRI images of a glioblastoma patient who was administered L19-TNF in accordance with the invention. The upper panel (A) is the initial (baseline) MRI image, which shows the glioblastoma indicated in the white circle. The lower panel (B) shows an MRI image taken following treatment, 40 days after the baseline image was taken. The glioblastoma shown in panel B is indicated with an arrow and white circle. It is substantially reduced.

DETAILED DESCRIPTION OF THE INVENTION

Certain aspects of the invention are as set out in the appended claims, which may be combined with any other part of the present disclosure.

An antibody molecule is an immunoglobulin whether natural or partly or wholly synthetically produced. The term also covers any polypeptide or protein comprising an antibody antigen-binding site. Thus, this term covers antibody fragments and derivatives, including any polypeptide comprising an antibody antigen-binding site, whether natural or wholly or partially synthetic. Fusion proteins comprising an antibody antigen-binding site, or equivalent, fused to another polypeptide are therefore included. Cloning and expression of chimeric antibodies is well known (EP0120694, EP0125023).

Further techniques available in the art of antibody engineering have made it possible to isolate human and humanised antibodies. For example, human hybridomas can be made as previously described. Phage display is another established technique (WO92/01047). Transgenic mice in which the mouse antibody genes are inactivated and functionally replaced with human antibody genes while leaving intact other components of the mouse immune system can be used for isolating human antibodies.

Synthetic antibody molecules may be created by expression from genes generated by means of oligonucleotides synthesised and assembled within suitable expression vectors.

It has been shown that fragments of a whole antibody can perform the function of binding antigens. Antibody fragments are preferred in conjugates of the invention owing to their small size and minimised interaction with other molecules and receptors (e.g. Fc receptor). Particularly preferred are single chain Fv molecules (scFv), wherein a VH domain and a VL domain are linked by a peptide linker which allows the two domains to associate to form an antigen binding site. scFv may be stabilised by the incorporation of disulphide bridges linking the VH and VL domains.

Another small antigen-binding antibody fragment is a dAb (domain antibody), namely the variable region of an antibody heavy or light chain. VH dAbs occur naturally in camelids (e.g. camel, llama) and may be produced by immunising a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation.

An antigen-binding site is the part of a molecule that specifically binds to and is complementary to all or part of the target antigen. In an antibody molecule it is referred to as the antibody antigen-binding site, and comprises the part of the antibody that specifically binds to and is complementary to all or part of the target antigen. Where an antigen is large, an antibody may only bind to a particular part of the antigen, which part is termed an epitope. An antibody antigen-binding site may be provided by one or more antibody variable domains. Preferably, an antibody antigen-binding site comprises an antibody light chain variable region (VL) and an antibody heavy chain variable region (VH).

The term "specific" may be used to refer to the situation in which one member of a specific binding pair will not show any significant binding to molecules other than its specific binding partner(s). The term is also applicable where e.g. an antigen-binding site is specific for a particular epitope that is carried by a number of antigens, in which case the antibody carrying the antigen-binding site will be able to bind to the various antigens carrying the epitope.

In immunoconjugates of the invention, the antibody molecule preferably binds an extracellular matrix component which is a marker of tumour growth. The extracellular matrix (ECM) is remodelled during tumour growth, and alternative splice variants of ECM components may be selectively expressed at the site of the lesion.

One example is fibronectin. For example, the B-FN isoform of fibronectin contains an extra domain ED-B. An antibody molecule preferably binds specifically to ED-B of fibronectin isoform B-FN. The antibody molecule may comprise the L19 CDRs. For example, the antibody molecule may be a scFv having a VH domain with an amino acid sequence comprising VH CDR1, VH CDR2 and/or VH CDR3 of L19, and a VL domain with an amino acid sequence comprising VL CDR1, VL CDR2 and/or VL CDR3 of L19. An antibody molecule may comprise a VH domain having an amino acid sequence with at least 60%, 65%, 70%, 75%, 80%, 85%, 90%, 95% or 100% sequence identity with the amino acid sequence of the L19 VH domain as set out in SEQ ID NO: 7, and/or comprises a VL domain having an amino acid sequence with at least 60%, 65%, 70%, 75%, 80%, 85%, 90%, 95% or 100% sequence identity with the amino acid sequence of the L19 VL domain as set out in SEQ ID NO: 9. Preferably the antibody molecule is an scFv(L19) comprising an L19 VH domain (SEQ ID NO: 7) and an L19 VL domain (SEQ ID NO: 9). In a preferred embodiment, the antibody molecule is L19(scFv) having the amino acid sequence SEQ ID NO: 10 (FIG. 2).

Modified forms of the L19 VH and/or VL domain may be employed in immunoconjugates of the invention, for example an antibody molecule may comprise the L19 VH or L19 VL domain in which 1, 2, 3, 4 or 5 amino acid substitutions have been made in a CDR and/or framework region, while retaining specific binding to fibronectin ED-B. Such amino acid substitutions are preferably conservative, e.g. substitution of one hydrophobic residue for another, one polar residue for another, arginine for lysine, glutamic for aspartic acid, or glutamine for asparagine.

Nucleic acid molecules encoding the immunoconjugates and parts thereof also form part of the invention. The nucleic acid molecule may be a vector, e.g. a plasmid suitable for expression of the nucleotide sequence. Normally the nucleotide sequence is operably linked to a regulatory element such as a promoter for transcription.

The nucleic acid molecules may be contained in a host cell, which may be a cell cotransfected with the nucleic acid molecules or a daughter of such a cell. Cells, especially eukaryotic cells e.g. HEK and CHO cells, or bacterial cells e.g. *Escherichia coli*, containing the nucleic acid molecules also form part of the invention.

Immunoconjugates of the invention may be produced using recombinant techniques, for example by expressing all or part of the immunoconjugate as a fusion protein. Normally the expression is performed in a host cell containing nucleic acid, as described above. Expression may therefore comprise culturing such a host cell. For TNFα fusion proteins, trimerisation of the subunits may occur in the cell or during purification of the fusion proteins from the cell.

Preferably the antibody molecule is conjugated with the cytokine by means of a peptide bond, e.g. within a fusion protein comprising the TNFα and the antibody molecule or a polypeptide chain thereof. See WO2001/062298. An example of a suitable linker is set out in SEQ ID NO: 12.

TNFα used in immunoconjugates of the invention is preferably human TNFα. The human TNFα preferably comprises or consists of the amino acid sequence set out in SEQ ID NO: 11. Antibody molecules are preferably human or humanised antibody molecules. The L19-huTNFα conjugate may comprise or consist of the amino acid sequence set out in SEQ ID NO: 13.

Also described is a method comprising formulating the immunoconjugate or immunoconjugates into a pharmaceutical composition. Generally, this involves purifying the immunoconjugate or immunoconjugates and combining it with a physiologically acceptable carrier.

Immunoconjugates and compositions in accordance with the present invention may comprise, in addition to the active ingredient (immunoconjugate), a pharmaceutically acceptable excipient, carrier, buffer, stabiliser or other materials well known to those skilled in the art. Such materials should be non-toxic and should not interfere with the efficacy of the active ingredient. For injection at the tumour site, the immunoconjugate may be in the form of a parenterally acceptable aqueous solution which is pyrogen-free and has suitable pH, isotonicity and stability.

The therapeutic uses and methods described herein can be applied to different types of brain tumor. The tumor may be any unwanted cell proliferation (or any disease manifesting itself by unwanted cell proliferation), neoplasm or tumor. For instance, the brain tumor could be a primary malignant neoplasm of brain, a secondary malignant neoplasm of brain, a secondary malignant neoplasm of brain and cerebral meninges, a benign neoplasm of brain and central nervous system or a neoplasm of uncertain behaviour of brain. The neoplasm may be a glioma.

Some embodiments of this invention involve the use of the TNF immunoconjugate administered in combination with chemotherapy. Chemotherapy may be based on alkylating agents such as, chlorambucil, melphalan, cyclophosphamide, chlormethine, uramustine, ifosfamide, bemdamustine, carmustine, lomustine, streptozocin, busulfan, procarbazine, dacarbazine and temozolomide. Chemotherapy may be also based on alkylating-like agents such as cisplatin, carboplatin, dicycloplatin, eptaplatin, lobaplatin, miriplatin, nedaplatin, oxalilatin, picoplatin, satraplatin, Some embodiments of this invention involve the use of the TNF immunoconjugate formulated as a pharmaceutical composition. Pharmaceutical compositions may include a pharmaceutically acceptable "excipient" composed of materials that are considered safe and effective. "Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. The excipients may include solvents, solubility enhancers, suspending agents, buffering agents, isotonicity agents, antioxidants or antimicrobial preservatives. Certain compositions of L19-TNFα are disclosed in WO2018/011404.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the description and examples should not be construed as limiting.

The present invention is illustrated by the following examples.

EXAMPLES

Example 1—Effect of L19-TNFα on Brain Tumour

Three patients with recurrent glioblastoma were treated with L19-TNFα at a dose level of 10 µg/kg. Already twenty-four hours after the infusion, a decrease in overall tumor perfusion and an emerging tumor necrosis was detected, as shown in FIG. 1A. One patient had progressive disease after three months and two patients still have stable disease with an increasing area of necrosis in the tumor region at six months after treatment. This is surprising considering that the Progression Free Survival (PFS) for recurrent glioblastoma is 1.5 months.

The patient with progressive disease underwent re-section and the tissue from this surgery, i.e. after treatment with L19-TNFα, was compared with the tissue obtained during first surgery. By immunohistochemistry, a significant increase in tumor-infiltrating CD4 and CD8 T-cells in the tumor after L19-TNFα treatment was detected. Furthermore, increased levels of cleaved caspase-3 were found suggesting a higher number of dead tumor cells, as shown in FIG. 1B. These data demonstrate the in situ activation due to the targeted delivery of TNF.

Example 2—Effect of L19-TNFα with Chemotherapy on Brain Tumour

This example describes the effect of a combination therapy on a patient with recurrent glioblastoma after chemoradiotherapy followed by temozolomide maintenance therapy.

A 61-year old male patient with glioblastoma (WHO grade IV) at first recurrence, received 90 mg/m2 lomustine (CCNU) on Day 1. Additionally, this patient received 13 μg/kg L19-TNF, by iv infusion, on Days 1, 3, 5, 22, 24 and 26.

The patient had been pretreated for newly diagnosed glioblastoma with resection and chemoradiotherapy followed by temozolomide maintenance therapy.

Contrast enhanced MRI was performed initially, before receiving the lomustine and L19-TNF (baseline image; see FIG. 3A) and 40 days after baseline image (FIG. 3B). The tumour was substantially reduced.

Numbered Paragraphs

1. A TNFα immunoconjugate for use in a method of treating a brain tumor in a patient, the method comprising administering the TNFα immunoconjugate to the patient.
2. The TNFα immunoconjugate for the use according to paragraph 1, wherein the brain tumor is a glioma.
3. The TNFα immunoconjugate for the use according to any one of the preceding paragraphs, wherein the TNFα immunoconjugate comprises TNFα linked to an antibody molecule that binds to a splice isoform of an extracellular matrix component.
4. The TNFα immunoconjugate for the use according to any one of the preceding paragraphs, wherein the antibody molecule binds a splice isoform of fibronectin which is B-FN.
5. The TNFα immunoconjugate for the use according to any one of the preceding paragraphs, wherein the TNFα immunoconjugate comprises TNFα linked to an antibody molecule comprising L19 complementarity determining regions (CDRs), wherein the L19 CDRs are:

```
VH CDR 1
                                SEQ ID NO: 1
SFSMS

VH CDR 2
                                SEQ ID NO: 2
SISGSSGTTYYADSVKG

VH CDR 3
                                SEQ ID NO: 3
PFPYFDY

VL CDR 1
                                SEQ ID NO: 4
RASQSVSSSFLA

VL CDR 2
                                SEQ ID NO: 5
YASSRAT

VL CDR 3
                                SEQ ID NO: 6
QQTGRIPPT.
```

6. The TNFα immunoconjugate for the use according to paragraph 5, wherein the antibody molecule comprises the L19 VH domain SEQ ID NO: 7 and the L19 VL domain SEQ ID NO: 9.
7. The TNFα immunoconjugate for the use according to any one of the preceding paragraphs, wherein the TNFα immunoconjugate comprises TNFα linked to an antibody molecule which is a scFv, optionally wherein the antibody molecule is L19 (scFv) as set forth in SEQ ID NO: 10.
8. The TNFα immunoconjugate for the use according to any one of the preceding paragraphs, wherein the TNFα immunoconjugate has an amino acid sequence of SEQ ID NO: 13.
9. The TNFα immunoconjugate for the use according to any one of the preceding paragraphs, wherein the immunoconjugate is administered by intravenous injection.
10. The TNFα immunoconjugate for the use according to paragraph 9, wherein the injection is intratumoural injection or intrathecal injection.
11. The TNFα immunoconjugate for the use according to any one of the preceding paragraphs, wherein the brain tumor is a Grade III/IV glioma.
12. The TNFα immunoconjugate for the use according to paragraph 11, wherein the glioma is isocitrate dehydrogenase (IDH) wildtype.
13. The TNFα immunoconjugate for the use according to paragraph 11 or paragraph 12, wherein the Grade III/IV glioma is at first relapse.
14. The TNFα immunoconjugate for the use according to paragraph 11 or paragraph 12, wherein the glioma is a Grade IV glioblastoma, which is newly diagnosed.
15. The TNFα immunoconjugate for the use according to any one of paragraphs 11 to 13, wherein the glioma is a Grade IV glioblastoma at first relapse.
16. The TNFα immunoconjugate for the use according any of the preceding paragraphs, wherein the immunoconjugate is administered in combination with chemotherapy and/or radiotherapy.
17. The TNFα immunoconjugate for the use according to paragraph 16, wherein the chemotherapy is the alkylating agent temozolomide (TMZ).
18. The TNFα immunoconjugate for the use according to paragraph 17, wherein temozolomide (TMZ) is administered at 75-200 mg/m$^2$.
19. The TNFα immunoconjugate for the use according to paragraph 17 or paragraph 18, wherein the radiotherapy is administered at a dose of 20-100 Gy, 40-80 Gy, or 60 Gy,
20. The TNFα immunoconjugate for the use according to paragraph 19, wherein the radiotherapy is administered at a dose of 60 Gy in fractions, preferably 60 Gy/30 fractions.

21. The TNFα immunoconjugate for the use according to paragraph 19 or 20, wherein the glioma is a newly diagnosed glioblastoma.

22. The TNFα immunoconjugate for the use according to paragraph 16, wherein the chemotherapy is the alkylating agent lomustine.

23. The TNFα immunoconjugate for the use according to paragraph 21, wherein lomustine is administered at a dose that is within the range of 50-200 mg/m², or 75-150 mg/m².

24. The TNFα immunoconjugate for the use according to paragraph 22, wherein the lomustine is administered at a dose of about 80, about 90, about 100, or about 110 mg/m².

25. The TNFα immunoconjugate for the use according to paragraph 22 or 23, wherein lomustine is administered at 90 mg/m².

25. The TNFα immunoconjugate for the use according to any one of paragraphs 22-25, wherein the glioblastoma is at first relapse.

26. The TNFα immunoconjugate for the use according to any one of the preceding paragraphs, wherein the method comprises subsequent administrations of the TNFα immunoconjugate.

27. The TNFα immunoconjugate for the use according any of the preceding paragraphs, wherein tumor necrosis is detectable one day after the TNFα immunoconjugate is administered to the patient.

28. The TNFα immunoconjugate for the use according any of the preceding paragraphs, wherein a reduction of blood perfusion to the tumor is detectable one day after the TNFα immunoconjugate is administered to the patient.

29. The TNFα immunoconjugate for the use according any of the preceding paragraphs, wherein the method induces infiltration of T cells into the tumor.

SEQUENCE LISTING

```
Amino acid sequence of L19 CDRs
L19 CDR1 VH
                                         (SEQ ID NO: 1)
SFSMS L19 CDR2 VH
                                         (SEQ ID NO: 2)
SISGSSGTTYYADSVKG

L19 CDR3 VH
                                         (SEQ ID NO: 3)
PFPYFDY

L19 CDR1 VL
                                         (SEQ ID NO: 4)
RASQSVSSSFLA

L19 CDR2 VL
                                         (SEQ ID NO: 5)
YASSRAT

L19 CDR3 VL
                                         (SEQ ID NO: 6)
QQTGRIPPT
```

```
-continued
Amino acid sequence of the L19 VH domain
                                         (SEQ ID NO: 7)
EVQLLESGGGLVQPGGSLRLSCAASGFTFSSFSMSWVRQAPGKGLEWVSS

ISGSSGTTYYADSVKGRFTISRDNSKNTLYLQMNSLRAEDTAVYYCAKPF

PYFDYWGQGTLVTVSS

Amino acid sequence of the linker between VH and
VL
                                         (SEQ ID NO: 8)
GDGSSGGSGGAS Amino acid sequence of the L19 VL domain
                                         (SEQ ID NO: 9)
EIVLTQSPGTLSLSPGERATLSCRASQSVSSSFLAWYQQKPGQAPRLLIY

YASSRATGIPDRFSGSGSGTDFTLTISRLEPEDFAVYYCQQTGRIPPTFG

QGTKVEIK

Amino acid sequence of the L19 scFv
                                         (SEQ ID NO: 10)
EVQLLESGGGLVQPGGSLRLSCAASGFTFSSFSMSWVRQAPGKGLEWVSS

ISGSSGTTYYADSVKGRFTISRDNSKNTLYLQMNSLRAEDTAVYYCAKPF

PYFDYWGQGTLVTVSSGDGSSGGSGGASEIVLTQSPGTLSLSPGERATLS

CRASQSVSSSFLAWYQQKPGQAPRLLIYYASSRATGIPDRFSGSGSGTDF

TLTISRLEPEDFAVYYCQQTGRIPPTFGQGTKVEIK

Amino acid sequence of the soluble form of the
extracellular domain of human TNFα(huTNFα).
                                         (SEQ ID NO: 11)
VRSSSRTPSDKPVAHVVANPQAEGQLQWLNRRANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL

Amino acid sequence of the linker between scFv and
TNF
                                         (SEQ ID NO: 12)
EFSSSSGSSSSGSSSSG Amino acid sequence of the L19-huTNF conjugate
                                         (SEQ ID NO: 13)
EVQLLESGGGLVQPGGSLRLSCAASGFTFSSFSMSWVRQAPGKGLEWVSS

ISGSSGTTYYADSVKGRFTISRDNSKNTLYLQMNSLRAEDTAVYYCAKPF

PYFDYWGQGTLVTVSSGDGSSGGSGGASEIVLTQSPGTLSLSPGERATLS

CRASQSVSSSFLAWYQQKPGQAPRLLIYYASSRATGIPDRFSGSGSGTDF

TLTISRLEPEDFAVYYCQQTGRIPPTFGQGTKVEIKEFSSSSGSSSSGSS

SSGVRSSSRTPSDKPVAHVVANPQAEGQLQWLNRRANALLANGVELRDNQ

LVVPSEGLYLIYSQVLFKGQGCPSTHVLLTHTISRIAVSYQTKVNLLSAI

KSPCQRETPEGAEAKPWYEPIYLGGVFQLEKGDRLSAEINRPDYLDFAES

GQVYFGIIAL
```

The invention claimed is:

1. A method of treating a brain tumor in a patient, comprising administering a TNFα immunoconjugate, the method comprising administering the TNFα immunoconjugate in combination with chemotherapy and radiotherapy to the patient, wherein the TNFα immunoconjugate comprises TNFα linked to an antibody molecule comprising L19 complementarity determining regions (CDRs), wherein the L19 CDRs are:

VH CDR1
SEQ ID NO: 1
SFSMS

VH CDR 2
SEQ ID NO: 2
SISGSSGTTYYADSVKG

VH CDR 3
SEQ ID NO: 3
PFPYFDY

VL CDR 1
SEQ ID NO: 4
RASQSVSSSFLA

VL CDR 2
SEQ ID NO: 5
YASSRAT

VL CDR 3
SEQ ID NO: 6
QQTGRIPPT, wherein the chemotherapy is temozolomide (TMZ), and wherein the brain tumor is a glioma.

2. The method of treatment according to claim 1, wherein the antibody molecule comprises the L19 VH domain SEQ ID NO: 7 and the L19 VL domain SEQ ID NO: 9.

3. The method of treatment according to claim 1, wherein the TNFα immunoconjugate comprises TNFα linked to L19 (scFv) as set forth in SEQ ID NO: 10.

4. The method of treatment according to claim 1, wherein the TNFα immunoconjugate has an amino acid sequence of SEQ ID NO: 13.

5. The method of treatment according to claim 1, wherein the immunoconjugate is administered by intravenous injection.

6. The according to claim 1, wherein the immunoconjugate is administered by intratumoural injection or intrathecal injection.

7. The according to claim 1, wherein the brain tumor is selected from a Grade III/IV glioma, a Grade III/IV glioma at first relapse, an isocitrate dehydrogenase (IDH) wildtype glioma, a Grade IV glioblastoma, a Grade IV glioblastoma at first relapse.

8. The according to claim 1, wherein temozolomide (TMZ) is administered at 75-200 mg/m2.

9. The method of treatment according to claim 1, wherein the radiotherapy is administered at 60 Gy/30 fractions.

10. The method of claim 1, wherein the method comprises subsequent administrations of the TNFα immunoconjugate.

11. A method of treating a glioma in a patient, comprising administering a TNFα immunoconjugate in combination with chemotherapy and radiotherapy to the patient, wherein the TNFα immunoconjugate comprises TNFα linked to an antibody molecule comprising L19 complementarity determining regions (CDRs), wherein the L19 CDRs are:

VH CDR1
SEQ ID NO: 1
SFSMS

VH CDR 2
SEQ ID NO: 2
SISGSSGTTYYADSVKG

VH CDR 3
SEQ ID NO: 3
PFPYFDY

VL CDR 1
SEQ ID NO: 4
RASQSVSSSFLA

VL CDR 2
SEQ ID NO: 5
YASSRAT,
and

VL CDR 3
SEQ ID NO: 6
QQTGRIPPT;

wherein the chemotherapy is temozolomide (TMZ);
wherein the antibody molecule comprises the L19 VH domain SEQ ID NO: 7 and the L19 VL domain SEQ ID NO: 9;
wherein the TNFα immunoconjugate comprises TNFα linked to L19 (scFv) as set forth in SEQ ID NO: 10 and the TNFα immunoconjugate has an amino acid sequence of SEQ ID NO: 13.

12. The method of claim 11, wherein the immunoconjugate is administered by a route selected from intravenous injection, intratumoural injection, and intrathecal injection.

13. The method of claim 11, wherein said glioma is selected from a Grade III/IV glioma, a Grade III/IV glioma at first relapse, an isocitrate dehydrogenase (IDH) wildtype glioma, a newly diagnosed glioblastoma, a newly diagnosed Grade IV glioblastoma, and a Grade IV glioblastoma at first relapse.

14. The method of claim 11, wherein temozolomide (TMZ) is administered at 75-200 mg/m$^2$.

15. The method of treatment according to claim 11, wherein the radiotherapy is administered at 60 Gy/30 fractions.

16. The method of claim 11 further comprising subsequent administrations of the TNFα immunoconjugate.

* * * * *

SEQUENCE LISTING

```
Sequence total quantity: 13
SEQ ID NO: 1                   moltype = AA  length = 5
FEATURE                        Location/Qualifiers
REGION                         1..5
                               note = synthetic construct
source                         1..5
                               mol_type = protein
                               organism = synthetic construct
SEQUENCE: 1
SFSMS                                                                           5

SEQ ID NO: 2                   moltype = AA  length = 17
FEATURE                        Location/Qualifiers
REGION                         1..17
                               note = synthetic construct
source                         1..17
                               mol_type = protein
                               organism = synthetic construct
SEQUENCE: 2
SISGSSGTTY YADSVKG                                                             17

SEQ ID NO: 3                   moltype = AA  length = 7
FEATURE                        Location/Qualifiers
REGION                         1..7
                               note = synthetic construct
source                         1..7
                               mol_type = protein
                               organism = synthetic construct
SEQUENCE: 3
PFPYFDY                                                                         7

SEQ ID NO: 4                   moltype = AA  length = 12
FEATURE                        Location/Qualifiers
REGION                         1..12
                               note = synthetic construct
source                         1..12
                               mol_type = protein
                               organism = synthetic construct
SEQUENCE: 4
RASQSVSSSF LA                                                                  12

SEQ ID NO: 5                   moltype = AA  length = 7
FEATURE                        Location/Qualifiers
REGION                         1..7
                               note = synthetic construct
source                         1..7
                               mol_type = protein
                               organism = synthetic construct
SEQUENCE: 5
YASSRAT                                                                         7

SEQ ID NO: 6                   moltype = AA  length = 9
FEATURE                        Location/Qualifiers
REGION                         1..9
                               note = synthetic construct
source                         1..9
                               mol_type = protein
                               organism = synthetic construct
SEQUENCE: 6
QQTGRIPPT                                                                       9

SEQ ID NO: 7                   moltype = AA  length = 116
FEATURE                        Location/Qualifiers
REGION                         1..116
                               note = synthetic construct
source                         1..116
                               mol_type = protein
                               organism = synthetic construct
SEQUENCE: 7
EVQLLESGGG LVQPGGSLRL SCAASGFTFS SFSMSWVRQA PGKGLEWVSS ISGSSGTTYY               60
ADSVKGRFTI SRDNSKNTLY LQMNSLRAED TAVYYCAKPF PYFDYWGQGT LVTVSS                 116

SEQ ID NO: 8                   moltype = AA  length = 12
FEATURE                        Location/Qualifiers
REGION                         1..12
                               note = synthetic construct
source                         1..12
                               mol_type = protein
```

```
                        organism = synthetic construct
SEQUENCE: 8
GDGSSGGSGG AS                                                           12

SEQ ID NO: 9            moltype = AA   length = 108
FEATURE                 Location/Qualifiers
REGION                  1..108
                        note = synthetic construct
source                  1..108
                        mol_type = protein
                        organism = synthetic construct
SEQUENCE: 9
EIVLTQSPGT LSLSPGERAT LSCRASQSVS SSFLAWYQQK PGQAPRLLIY YASSRATGIP        60
DRFSGSGSGT DFTLTISRLE PEDFAVYYCQ QTGRIPPTFG QGTKVEIK                    108

SEQ ID NO: 10           moltype = AA   length = 236
FEATURE                 Location/Qualifiers
REGION                  1..236
                        note = synthetic construct
source                  1..236
                        mol_type = protein
                        organism = synthetic construct
SEQUENCE: 10
EVQLLESGGG LVQPGGSLRL SCAASGFTFS SFSMSWVRQA PGKGLEWVSS ISGSSGTTYY        60
ADSVKGRFTI SRDNSKNTLY LQMNSLRAED TAVYYCAKPF PYFDYWGQGT LVTVSSGDGS       120
SGGSGGASEI VLTQSPGTLS LSPGERATLS CRASQSVSSS FLAWYQQKPG QAPRLLIYYA       180
SSRATGIPDR FSGSGSGTDF TLTISRLEPE DFAVYYCQQT GRIPPTFGQG TKVEIK           236

SEQ ID NO: 11           moltype = AA   length = 157
FEATURE                 Location/Qualifiers
REGION                  1..157
                        note = synthetic construct
source                  1..157
                        mol_type = protein
                        organism = synthetic construct
SEQUENCE: 11
VRSSSRTPSD KPVAHVVANP QAEGQLQWLN RRANALLANG VELRDNQLVV PSEGLYLIYS        60
QVLFKGQGCP STHVLLTHTI SRIAVSYQTK VNLLSAIKSP CQRETPEGAE AKPWYEPIYL       120
GGVFQLEKGD RLSAEINRPD YLDFAESGQV YFGIIAL                                157

SEQ ID NO: 12           moltype = AA   length = 17
FEATURE                 Location/Qualifiers
REGION                  1..17
                        note = synthetic construct
source                  1..17
                        mol_type = protein
                        organism = synthetic construct
SEQUENCE: 12
EFSSSSGSSS SGSSSSG                                                       17

SEQ ID NO: 13           moltype = AA   length = 410
FEATURE                 Location/Qualifiers
REGION                  1..410
                        note = synthetic construct
source                  1..410
                        mol_type = protein
                        organism = synthetic construct
SEQUENCE: 13
EVQLLESGGG LVQPGGSLRL SCAASGFTFS SFSMSWVRQA PGKGLEWVSS ISGSSGTTYY        60
ADSVKGRFTI SRDNSKNTLY LQMNSLRAED TAVYYCAKPF PYFDYWGQGT LVTVSSGDGS       120
SGGSGGASEI VLTQSPGTLS LSPGERATLS CRASQSVSSS FLAWYQQKPG QAPRLLIYYA       180
SSRATGIPDR FSGSGSGTDF TLTISRLEPE DFAVYYCQQT GRIPPTFGQG TKVEIKEFSS       240
SSGSSSSGSS SSGVRSSSRT PSDKPVAHVV ANPQAEGQLQ WLNRRANALL ANGVELRDNQ       300
LVVPSEGLYL IYSQVLFKGQ GCPSTHVLLT HTISRIAVSY QTKVNLLSAI KSPCQRETPE       360
GAEAKPWYEP IYLGGVFQLE KGDRLSAEIN RPDYLDFAES GQVYFGIIAL                  410
```